(12) United States Patent
Zhu et al.

(10) Patent No.: US 8,143,019 B2
(45) Date of Patent: Mar. 27, 2012

(54) PORTABLE MICROBIOLOGICAL TESTING DEVICE FOR GASES

(75) Inventors: Xiangyang Zhu, Lake Zurich, IL (US); Kristine Mila H. Cruz, Chicago, IL (US); Diane Saber, Kildeer, IL (US)

(73) Assignee: Gas Technology Institute, Des Plaines, IL (US)

( * ) Notice: Subject to any disclaimer, the term of this patent is extended or adjusted under 35 U.S.C. 154(b) by 298 days.

(21) Appl. No.: 12/494,801

(22) Filed: Jun. 30, 2009

(65) Prior Publication Data
US 2010/0330603 A1 Dec. 30, 2010

(51) Int. Cl.
*C12Q 1/02* (2006.01)
*C12Q 1/04* (2006.01)

(52) U.S. Cl. ............................. 435/34; 435/29

(58) Field of Classification Search .......................... None
See application file for complete search history.

(56) References Cited

U.S. PATENT DOCUMENTS 5,874,237 A * 2/1999 Hull et al. ........................ 435/34
2004/0002126 A1 * 1/2004 Houde et al. ................. 435/7.32

OTHER PUBLICATIONS

Gerhardt et al. In: "Manual of Methods for General Bacteriology". 1981, p. 179.*
Atlas R. In: "Handbook of Microbiological Media", 1993, pp. 556, 557, 709, 919.*
Cown et al. "The critical orifice liquid impinge as a sampler for bacterial aerosols". Appl. Microbiol. 1957, 5(2):119-124.*

* cited by examiner

*Primary Examiner* — Vera Afremova
(74) *Attorney, Agent, or Firm* — Mark E. Fejer

(57) ABSTRACT

A method and apparatus for microbiological testing of biogas and other gaseous streams in which a liquid bacteria growth medium disposed within a lower region of a portable sampling vessel is contacted with a gas sample of interest. The gas sample is passed through a hydrophobic filter element which retains microorganisms in the gas sample. The sampling vessel is then inverted, thereby submerging the hydrophobic filter element in the liquid bacteria growth medium. The sampling vessel is incubated for a predetermined period of time at a predetermined temperature following which a presence or absence of microorganisms is determined based on turbidity and/or color of the liquid bacteria growth medium.

Figure 1:
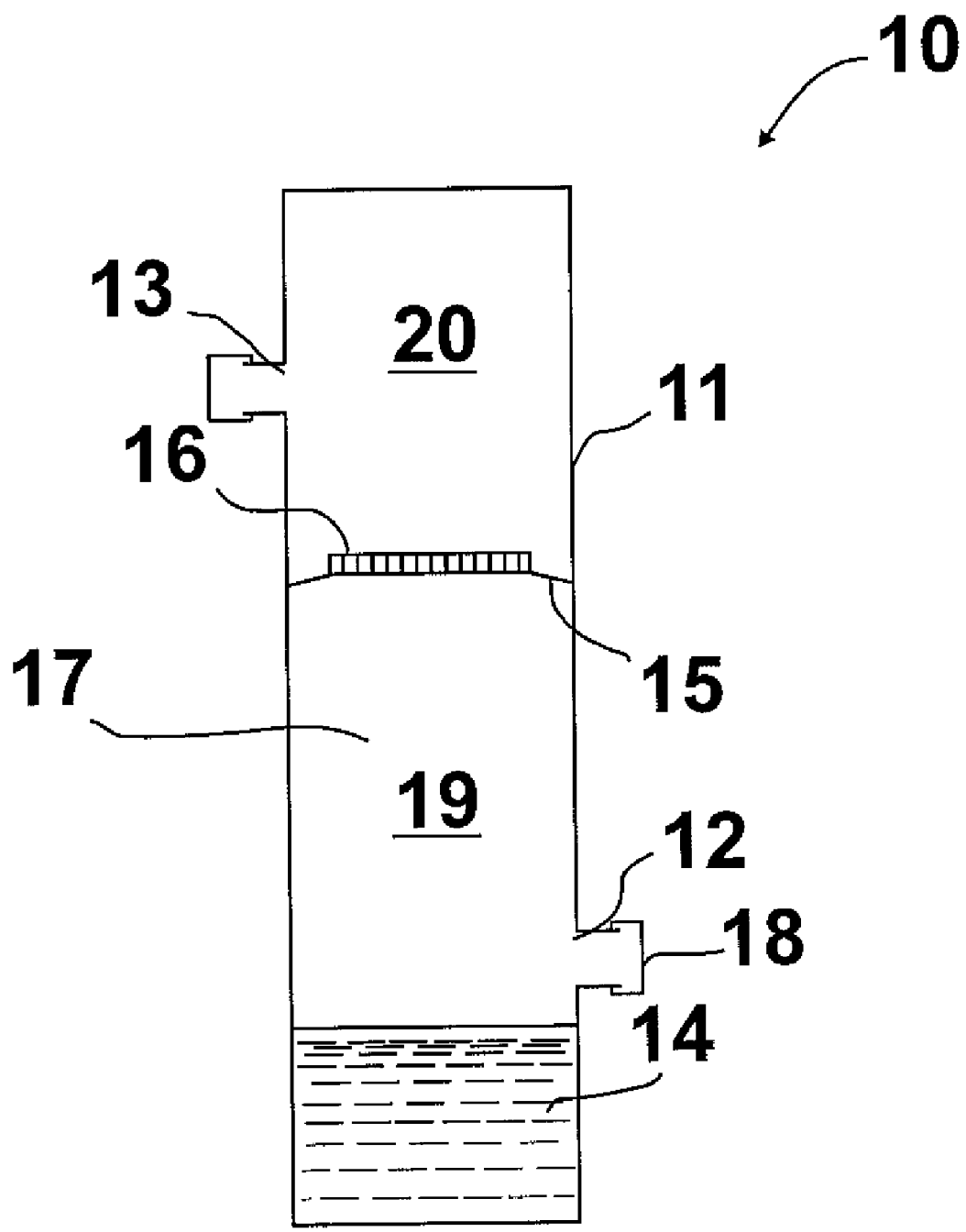
Figure 2:
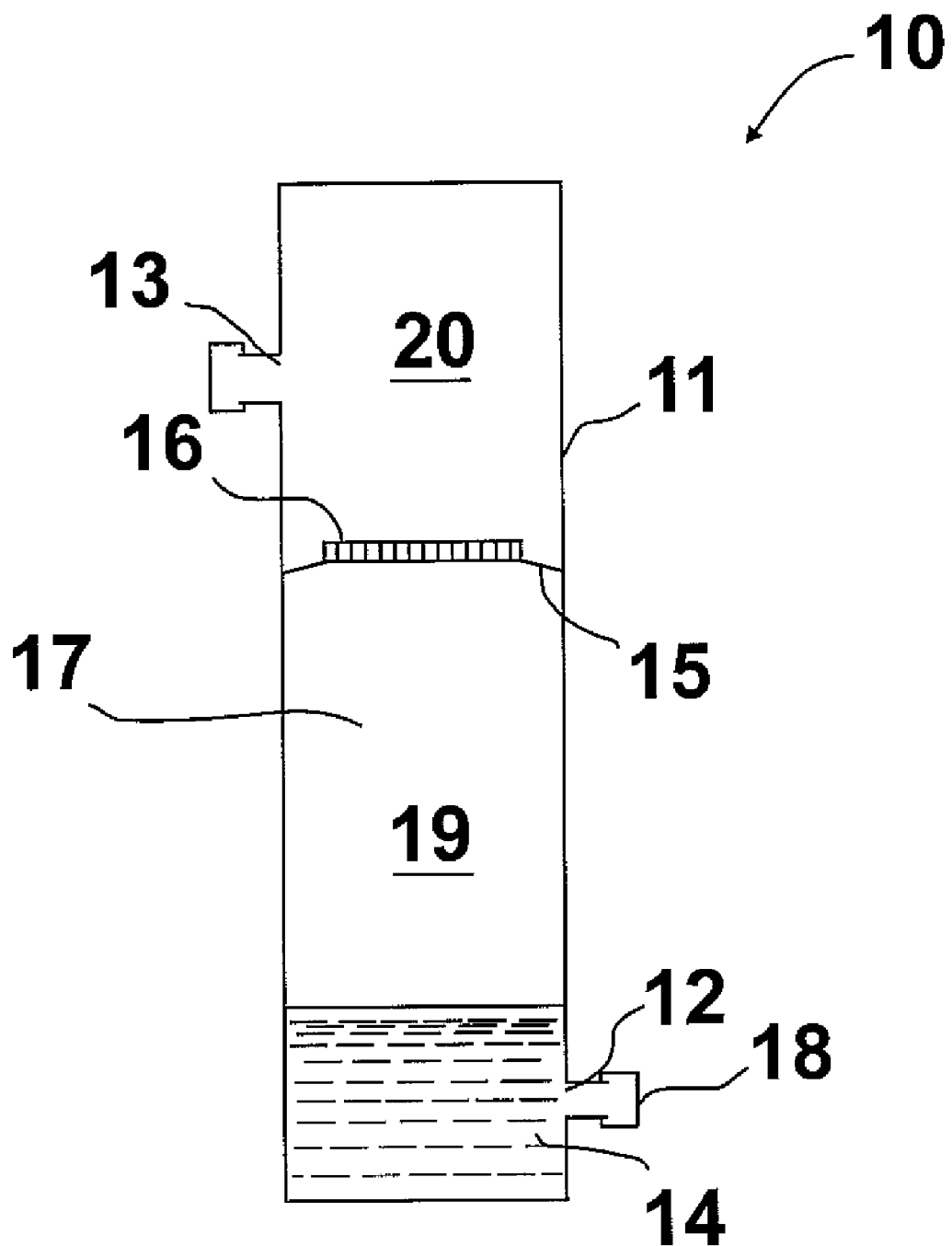

7 Claims, 2 Drawing Sheets

PORTABLE MICROBIOLOGICAL TESTING DEVICE FOR GASES

BACKGROUND OF THE INVENTION

1. Field of the Invention

This invention relates to a method and apparatus for detecting the presence of live microorganisms in gaseous streams. In one aspect, this invention relates to a portable apparatus for detecting the presence of live microorganisms in gaseous streams. In one aspect, this invention relates to a method and apparatus for detecting the presence of live microorganisms in gaseous streams produced by renewable energy sources, such as biogas and biomethane (a high methane content biogas) gas streams. In one aspect, this invention relates to a method and apparatus for detecting live microorganisms including, but not limited to, heterotrophic anaerobic bacteria, sulfate-reducing bacteria (SRB), acid-producing bacteria (APB), heterotrophic aerobic bacteria, and other types of culturable organisms having distinct metabolic characteristics as an indicator of positive growth.

2. Description of Related Art

As used herein, the term "biogas" refers to gases produced from renewable organic materials, also referred to as biomass, such as wood, agricultural crops or wastes, and municipal wastes. Biogas is produced from anaerobic degradation/digestion of organic matter, a process in which bacteria convert degradable organic matter into methane and carbon dioxide with smaller amounts of hydrogen sulfide, ammonia, and other trace components. Depending on the biomass source materials, produced biogas may contain constituents and compounds that pose hazards to human health, the environment, and safety. In addition, insufficiently processed biogas may contain trace or residual compounds that may compromise the integrity and operation of gas utilization equipment and/or natural gas pipeline systems. One such concern is the microorganisms which may be carried over from anaerobic digestion and which have survived the cleaning processes. When introduced into pipelines, some microorganisms may pose a corrosion risk to the pipelines. Thus, it is important that the overall microorganism load and major corrosion-causing microorganisms in biogas be identified, monitored, and removed prior to introduction of the biogas into existing natural gas supplies to avoid potential problems.

Conventional air sampling for the detection of microbes typically requires special equipment and highly trained personnel in specialized laboratories. In the U.S. pharmaceutical and medical industry, the most common air monitoring practice involves the use of impaction and centrifugal air samplers to collect a predetermined volume of air by passing the air sample through a microbial sampler and impacting the microorganisms in the air sample against agar-based microbial growth medium. Once the sample has been collected, the medium is incubated at a certain temperature for a predetermined period of time for detection and colony count of target microorganisms. For this purpose, there are a number of commercially available samplers designed for use in cleanroom environments. Slit-to-agar samplers, sieve impactors, sterilizable microbiological atrium, surface air system sampler, and MAS-100 microbial air monitoring systems are all commercially available samplers having similar design and sampling mechanisms. In each system or device, the sampler consists of a container designed to accommodate a Petri dish containing nutrient agar. A vacuum pump or fan draws a known volume of air through small holes or slits at the top of the sampler, and the particles in the air containing microorganisms impact on the agar medium in the Petri dish. The colonies are counted after the proper incubation period. The impaction speed as well as the particle size efficiency is a function of the diameter of the holes in the perforated lid and the speed of the fan. These samplers with high air flow rates generally allow for efficient impaction of particles 0.5 microns or larger in diameter, which is one of the major limitations for this type of technology, since many bacteria are smaller than 0.5 microns in diameter and, thus, cannot be efficiently captured by nutrient plates. In addition, the required high air flow, on the order of about one (1) cubic foot per minute, is not always possible to achieve in renewable gas lines, thereby further biasing the impaction toward the selection of larger particles. Finally, air flow desiccates the nutrient plate, limiting the maximum air sample volume that is allowed to pass each nutrient plate.

In centrifugal samplers, a propeller or turbine is used to pull a known volume of air into the unit and propel the air outward to impact on a tangentially disposed nutrient agar strip set on a flexible plastic base. However, the centrifugal air samplers disturb laminar airflow patterns and have been shown to have selectivity for larger particles as well, resulting in overestimation of the total airborne counts.

In liquid impingers, air is aspirated into a liquid and the microorganisms retained in the liquid are captured on a membrane filter through filtration and transferred to media plates to evaluate growth. The major shortcoming of the liquid impingement method is that the air bubbles in the headspace of the medium container burst and the majority of microorganisms in the air sample are not retained in the liquid medium. The retention rate of microorganisms is significantly affected by the volume of liquid medium (or the length of the path the bubbles travel in the liquid) and the size of bubbles generated during impingement. In addition, the multiple handling steps during sample collection may result in false positive results due to contamination.

In gelatin filtration, a gelatin filter is used to retain airborne microorganisms in the air pulled in by a vacuum pump. After a specific exposure time, the filter is aseptically removed and dissolved in an appropriate diluent and then plated on an appropriate agar medium to estimate its microbial content. Similar to nutrient plate sampling, the desiccation caused by the air flow limits the maximum air sample volume, and the larger pore size of the gelatin filter results in a bias towards larger particles and a lower recovery rate of microorganisms. In addition, as with the liquid impinger method, the multiple handling steps during sample collection may result in false positive results due to contamination.

SUMMARY OF THE INVENTION

It is, thus, one object of this invention to provide a method and apparatus for microbiological testing of gas samples which addresses issues associated with conventional testing methods as discussed herein above.

It is another object of this invention to provide a method and apparatus for microbiological testing of gas samples which is portable, thus, being suitable for use in the field, i.e. non-laboratory settings.

It is yet another object of this invention to provide a method and apparatus for microbiological testing of gas samples which is suitable for use in the field by a technician having minimal training in microbiology.

These and other objects of this invention are addressed by an apparatus for microbiological testing of renewable gases comprising a portable sampling vessel enclosing a space having an upper region and a lower region and forming a sample inlet in direct fluid communication with the lower region and forming a sample outlet in direct fluid communication with the upper region. As used herein, the term "direct fluid communication" means that there is no intervening element between the openings and the regions for fluid communication. A hydrophobic filter element is disposed within the sampling vessel, separating the upper and lower regions. A liquid bacteria growth medium is provided in the lower region in an amount such that the ratio of the height of headspace, i.e. distance between the liquid bacteria growth medium and the hydrophobic filter, to the height of medium in the lower region is greater than or equal to about 1:1.

In the method of this invention, a liquid bacteria growth medium disposed within a lower region of a portable sampling vessel, which lower region is separated from an upper region within the sampling vessel by a hydrophobic filter element, is contacted with a gas sample of interest. Thereafter, the gas sample is passed through the hydrophobic filter element whereby microorganisms in the gas sample are retained on the hydrophobic filter element. In accordance with one preferred embodiment, the gas sample is passed through the liquid bacteria growth medium and hydrophobic filter element whereby microorganisms in the gas sample are retained in the liquid medium as well as on the hydrophobic filter element. The sampling vessel is then inverted, thereby submerging the filter element in the liquid bacteria growth medium. The sampling vessel is incubated for a predetermined period of time at a predetermined temperature following which a presence of the microorganisms is determined based on turbidity and/or color of the liquid bacteria growth medium.

Although not limited thereto, target microorganisms for detection utilizing the method and apparatus of this invention include heterotrophic anaerobic bacteria, sulfate-reducing bacteria, and acid-producing bacteria. The presence of heterotrophic anaerobic bacteria is indicative of the cleanness of biogas products, and the presence of sulfate-reducing bacteria and acid-producing bacteria is indicative of the risk of microbial corrosion of the pipeline when biogas is introduced into the pipeline. The detection mechanism for heterotrophic anaerobic microorganisms is that thioglycolate medium (TGC) turns turbid after incubation at a suitable temperature for a suitable period of time, indicating the positive growth of general anaerobic microorganisms. The indicator for positive sulfate-reducing bacteria detection is that the color of modified Postgate Medium B medium (MPB) turns black after incubation at a suitable temperature for a suitable period of time. The indicator for positive acid-producing bacteria detection is that phenol red dextrose broth medium (PRD) turns turbid with color change from orange to yellow after incubation at a suitable temperature for a suitable period of time.

Several advantages compared with conventional microbiological testing methods are provided by the method and apparatus of this invention. Bacteria growth media are selective liquid media for corresponding microorganisms of interest, thereby improving the detection of the target microbes in the gas samples. One step handling minimizes the chances of sample contamination and reduces false positives. The gas sample impinges the liquid bacteria growth medium and then passes through the hydrophobic filter, dramatically improving the retention rate of microorganisms in the gas sample. Incubation is carried out with the apparatus in an inverted disposition with the hydrophobic filter submerged under the liquid bacteria growth medium, resulting in growth of retained microbes both on the filter and in the liquid growth medium, thereby improving the detection sensitivity of target microorganisms. The combination of liquid impingement and a filter improves the retention rate of live microorganisms passing through the sampling device by a magnitude of 1 to 2 compared with the retention rates resulting from the use of either alone. The apparatus is field-oriented, disposable after addition of bleach, and can be operated by a technician with minimal or no training in microbiology. And, finally, no additional equipment is required for sampling if the sampling line has sufficient positive pressure to push the gas sample through the liquid growth medium and filter.

BRIEF DESCRIPTION OF THE DRAWINGS

These and other objects and features of this invention will be better understood from the following detailed description taken in conjunction with the drawings wherein:

FIG. 1 is a schematic diagram of an apparatus in accordance with one embodiment of this invention; and FIG. 2 is a schematic diagram of an apparatus in accordance with another embodiment of this invention.

DETAILED DESCRIPTION OF THE PRESENTLY PREFERRED EMBODIMENTS

The invention disclosed herein is an apparatus 10 for microbiological testing of gas samples, shown in accordance with one embodiment in FIG. 1, comprising a portable sampling vessel 11 enclosing a sampling space having an upper region 20 and a lower region 19. The sampling vessel forms at least one gas sample inlet 12 in direct fluid communication with lower region 19 and at least one gas sample outlet 13 in direct fluid communication with upper region 20. Each of the sample inlets and sample outlets are closed off by a rubber cap 18 to enable maintaining of the gas sample within the sampling vessel during the incubation period. Disposed within the lower region of the sampling vessel is a liquid bacteria growth medium 14 suitable for growing the target microorganisms. Upper and lower regions 20 and 19 are separated by a hydrophobic filter element 15 disposed on a support 16, such as a screen material. In accordance with one embodiment of this invention, hydrophobic filter element 15 comprises a polytetrafluoroethylene (PTFE) membrane having a pore size of about 0.2 microns. As shown in FIG. 1, the at least one gas sample inlet 12 is disposed above the surface of the liquid bacteria growth medium 14 such that the gas sample entering the portable sampling vessel impacts upon the surface of the liquid medium before passing through the hydrophobic filter element. In accordance with another embodiment, shown in FIG. 2, the gas sample inlet is disposed below the surface of the liquid medium, as a result of which the gas sample passes through the liquid medium as it is introduced into the lower region 19 of the sample vessel and through the hydrophobic filter element into the upper region 20.

As shown in FIGS. 1 and 2, the lower region 19 comprises two portions, one of which is filled with the liquid bacteria growth medium and the other of which is the space between the surface of the liquid bacteria growth medium and the hydrophobic filter 15, which space is referred to herein as headspace. The size of the headspace is a function of, among other things, the amount of foaming that occurs during the gas sampling process. The size of the headspace should be sufficient to prevent clogging of the hydrophobic filter and the reduction of gas sample flow rate by any foaming that might occur. Preferably, the headspace is sized such that the ratio of the height of the headspace to the height of the liquid bacteria growth medium is at least 1:1. In accordance with one preferred embodiment, the ratio of headspace to liquid medium is in the range of about 1:1 to about 9:1.

In accordance with one exemplary embodiment, the apparatus of this invention was constructed of a 7-inch long tube having an inside diameter of about 1 3/16 inches. The tube was separated into two compartments using a hydrophobic filter element (PTFE filter, 0.2 μm pore size, 25 mm diameter). The headspace to medium ratio was about 6:1. 15 ml of liquid bacteria growth medium was added to the lower region just before sampling. The gas sample was introduced into the lower region so as to impinge or pass through the liquid medium, after which the gas sample passed through the hydrophobic filter into the upper region from which it passed out of the sampling vessel through the sample gas outlet. To reduce the amount of foaming, up to about 50 ppm of Antifoam 204 (Sigma Catalog #A8311) was added to the liquid growth medium.

As previously indicated, the method and apparatus of this invention are suitable for detecting any culturable organisms having distinct metabolic characteristics as an indicator of positive growth; and, as previously indicated, the microorganisms of interest associated with biogas streams are heterotrophic anaerobic bacteria, sulfate-reducing bacteria (SRB), and acid-producing bacteria (APB).

For the detection of heterotrophic anaerobic bacteria, the preferred liquid bacteria growth medium is thioglycolate medium (TGC). This medium turns turbid after incubation at 37° C. for seven (7) days or less, indicating positive growth of general anaerobic bacteria.

TGC Production

| Yeast extract | 5.0 g |
|---|---|
| Casitone | 15.0 g |
| Sodium chloride | 2.5 g |
| Thioglycolic acid | 0.3 ml |
| Dextrose | 5.0 g |
| Distilled water | 1000 ml |

Adjust the pH to 7.0 with 5 M NaOH; purge with oxygen-free $N_2$; autoclave at 121° C. for 15 minutes at 15 psi in a sealed container; and store the resulting medium at 4° C.

For the detection of sulfate-reducing bacteria (SRB), the preferred liquid bacteria growth medium is modified Postgate Medium B medium (MPB). This medium turns black after incubation at 37° C. for 14 days, indicating positive growth of SRB.

MPB Production

Solution A

| $KH_2PO_4$ | 0.5 g |
|---|---|
| $NH_4Cl$ | 1.0 g |
| $Na_2SO_4$ | 1.0 g |
| $CaCl_2 \cdot 2H_2O$ | 0.1 g |
| $MgSO_4 \cdot 7H_2O$ | 2.0 g |
| Sodium lactate solution (60%) | 5.0 ml |
| Sodium acetate | 2.5 g |
| Yeast extracts | 1.0 g |
| Distilled water | 997 ml |

All visible particles should be dissolved into the solution as best as possible through swirling (applying heat if necessary). The pH is adjusted to 7.0 with 2 M $H_2SO_4$ or 5 M KOH followed by purging with oxygen-free $N_2$. The resulting solution is autoclaved at 121° C. for 15 minutes at 15 psi in a sealed container and stored at 4° C.

Solution B

| Sodium thioglycolate | 10 g |
|---|---|
| Sodium ascorbate | 10 g |
| Distilled water | 100 ml |

The mixture is filter sterilized, aliquots distributed into sealed, $N_2$ purged and autoclaved tubes or bottles, and stored at 4° C.

Solution C

| $FeSO_4 \cdot 7H_2O$ | 27 g |
|---|---|
| Distilled water | 100 ml |

The mixture is filter sterilized and stored at room temperature. After creation of the solutions, 997 ml of Solution A, 1 ml of Solution B, and 1.85 ml of Solution C are mixed aseptically and anaerobically. To reduce precipitation, the medium should be brought to room temperature before adding Solution C.

For the detection of acid-producing bacteria (APB), the preferred liquid bacteria growth medium is anaerobic phenol red dextrose broth (PRD). This medium turns from orange to yellow with turbidity after incubation at 37° C. for seven (7) days or less, indicating positive growth of anaerobic APB.

PRD Production

| Beef extract | 1.0 g |
|---|---|
| Peptone | 10.0 g |
| Phenol Red | 0.018 g |
| Dextrose | 5.0 g |
| NaCl | 5.0 g |
| Distilled water | 1000 ml |

Adjust pH to 7.0 with 5 M NaOH; purge with oxygen-free $N_2$; autoclave at 121° C. for 15 minutes at 15 psi in a sealed container; and store at 4° C.

EXAMPLE 1

In this example, *Clostridium acetobutylicum* (ATCC 824) culture (pH 4.54) was washed with phosphate buffered saline (PBS, pH 7.0), and inoculated to PRD medium (orange) with a starting pH of 6.89. After two days of incubation at 37° C., the culture pH dropped to 5.24, and the culture was yellow in color with turbidity. The results were confirmed using three grown cultures prepared from 0.2 μm filters passed with raw biogas. The results indicated that PRD medium is appropriate for selective growth of APB in the samples, and the indicator (color change and turbidity) worked properly for the detection of APB in the samples. PRD medium shows significant color change when pH drops from approximately 6.7 to 6.1 or lower. The APB-containing environmental samples (e.g. biogas) reduce the medium pH to 5.3-6.1, which is enough to change the PRD medium color.

EXAMPLE 2

In this example, the tubular apparatus of this invention described herein above was tested with spiked natural gas.

*Comamonas denitrificans* (ATCC 700936) and *C. acetobutylicum* were used as model microbes for general bacteria and APB, respectively. 400 L of natural gas were bubbled through the growth bacteria cultures and introduced through the gas sample inlet into the apparatus. The spiked bacteria in the aerosol were retained on the filter. After sampling, the medium compartment of filter units was added with 30 ml of corresponding media for general bacteria or APB. The units were incubated upside down at 37° C., aerobically for *C. denitrificans* and anaerobically for *C. acetobutylicum*. The indicating signs were observed in all units after two days of incubation, i.e turbidity in the general bacteria unit and color change plus turbidity in the APB unit. The results from this test indicated that 1) hydrophobic PTFE gas filters will not leak during incubation, and 2) indicators for the detection of target bacteria work properly.

Based on laboratory testing data, 150-250 L of biogas or biomethane sample is the optimal sampling volume for use in accordance with the method and apparatus of this invention. The sampling apparatus should be able to accommodate gas sample flow rates as high as 5-10 L/min during sampling in order to reduce the sampling time to a reasonable level. However, a significant problem with operating at higher gas sampling flow rates is the formation and buildup of foam in the apparatus during gas sampling, which reduces the flow rate and eventually blocks the filter and stops the gas flow. Accordingly, in accordance with one preferred embodiment of this invention, an anti-foaming agent is incorporated into the liquid bacteria growth medium to reduce the amount of foaming that occurs at high gas sampling flow rates. Any anti-foaming agent which does not interfere with successful operation of the method and apparatus of this invention may be employed. Such anti-foaming agents are preferably colorless, clear, organic-based liquids which are not toxic to bacteria growth. One such anti-foaming agent is Antifoam 204, Catalog #A8311, available from Sigma-Aldrich Company. Not only is this anti-foaming agent not toxic to bacteria growth, at least up to a concentration of 50 ppm, but instead it stimulates the bacteria growth in the early stage, thereby shortening the incubation period needed for the detection of target microorganisms using the apparatus of this invention. 20-30 ppm of Antifoam 204 in the liquid bacteria growth medium is capable of providing enough anti-foaming capacity at a flow rate of 6 L/min to break the bubbles and prevent the bubbles from clogging the filter and sampling apparatus.

EXAMPLE 3

In this example, the apparatus of this invention was used for testing landfill biogas in the field. 15 ml of TGC medium containing 30 ppm of Antifoam 204 was added to the apparatus just prior to gas sampling. The average flow rate was maintained at 2.15 L/min during the sampling of 150 L of the landfill biogas. 30 ppm of Antifoam 204 in the TGC medium provided sufficient capacity to break the bubbles at a mark of 60 ml headspace of the apparatus. The apparatus was anaerobically incubated upside down at 37° C. After five (5) days, the culture turned turbid, indicating the apparatus successfully detected the presence of heterotrophic anaerobic bacteria in the cleaned landfill gas.

While in the foregoing specification this invention has been described in relation to certain preferred embodiments thereof and many details have been set forth for purpose of illustration, it will be apparent to those skilled in the art that the invention is susceptible to additional embodiments and that certain of the details described herein can be varied considerably without departing from the basic principles of the invention.

We claim:

1. A method for microbiological testing of gases comprising the steps of:
    contacting a liquid bacteria growth medium for microorganisms of interest disposed within a lower region of a portable sampling vessel with a gas sample of interest, said lower region separated from an upper region within said sampling vessel by a hydrophobic filter element and having a headspace above said liquid bacteria growth medium sized to provide a headspace to liquid ratio of one of greater than and equal to about 1:1;
    passing said gas sample of interest through said hydrophobic filter element whereby said microorganisms in said gas sample of interest are retained on said hydrophobic filter element;
    inverting said sampling vessel, thereby submerging said hydrophobic filter element in said liquid bacteria growth medium;
    incubating said sampling vessel for a predetermined period of time at a predetermined temperature; and
    determining a presence of said microorganisms based on at least one of turbidity and color of said liquid bacteria growth medium.

2. The method of claim 1, wherein said gas sample of interest is passed through said liquid bacteria growth medium before passing through said hydrophobic filter element.

3. The method of claim 1, wherein said gas sample of interest impacts on a surface of said liquid bacteria growth medium before passing through said hydrophobic filter element.

4. The method of claim 1, wherein said headspace to medium ratio is in a range of about 1:1 to about 9:1.

5. The method of claim 1, wherein said liquid bacteria growth medium comprises at least one anti-foaming agent.

6. The method of claim 1, wherein said sample gas is a biogas.

7. The method of claim 1, wherein said liquid bacteria growth medium is selected from the group consisting of thioglycolate medium (TGC), modified Postgate Medium B medium (MPB), phenol red dextrose broth medium (PRD), and mixtures thereof.

* * * * *